US008892216B2

(12) United States Patent
Leven

(10) Patent No.: US 8,892,216 B2
(45) Date of Patent: Nov. 18, 2014

(54) LEAD ANCHOR AND RELATED METHODS OF USE

(71) Applicant: Boston Scientific Neuromodulation Corporation, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/937,937

(22) Filed: Jul. 9, 2013

(65) Prior Publication Data

US 2014/0018884 A1 Jan. 16, 2014

Related U.S. Application Data

(60) Provisional application No. 61/670,337, filed on Jul. 11, 2012.

(51) Int. Cl.
*A61N 1/05* (2006.01)
(52) U.S. Cl.
CPC ............ *A61N 1/05* (2013.01); *A61N 2001/0582* (2013.01); *A61N 1/0558* (2013.01)
USPC ........................................... 607/119; 604/175
(58) Field of Classification Search
USPC ................................... 604/175; 607/116, 119
See application file for complete search history.

(56) References Cited

U.S. PATENT DOCUMENTS

| 6,181,969 | B1 | 1/2001 | Gord |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,672,734 | B2 | 3/2010 | Anderson et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,140,172 | B1 * | 3/2012 | Jones et al. .................. 607/126 |
| 8,175,710 | B2 | 5/2012 | He |
| 8,364,278 | B2 | 1/2013 | Pianca et al. |
| 2007/0150036 | A1 | 6/2007 | Anderson |

* cited by examiner

*Primary Examiner* — George Evanisko
(74) *Attorney, Agent, or Firm* — Lowe Graham Jones PLLC; Bruce E. Black

(57) ABSTRACT

A lead anchor includes a core housing defining a cavity; a swivel anchor disposed in the cavity and having a tubular portion and a locking portion; at least two locking members; and at least two sleeves with a portion of each of the sleeves and each of the locking members disposed within the cavity at a periphery of the cavity. The tubular portion is adapted to receive an external tool to rotate the swivel anchor within the cavity. The lead anchor has an unlocked configuration, in which the swivel anchor can rotate within the cavity of the core housing without compressing the sleeves, and a locked configuration, in which opposing ends of the locking portion of the swivel anchor each lie between one of the sleeves and one of the locking members and compress the sleeves and any lead disposed within the sleeves to hold that lead in place.

20 Claims, 7 Drawing Sheets

LEAD ANCHOR AND RELATED METHODS OF USE

CROSS-REFERENCE TO RELATED APPLICATIONS

This application claims the benefit under 35 U.S.C. §119(e) of U.S. Provisional Patent Application Ser. No. 61/670,337 filed on Jul. 11, 2012, which is incorporated herein by reference.

FIELD

The present invention is directed to the area of implantable stimulation systems and lead anchors for the implantable stimulation systems. The present invention is also directed to the method of manufacture and use of the implantable stimulation systems and the lead anchors.

BACKGROUND

Implantable stimulation systems have proven therapeutic in a variety of diseases and disorders. For example, spinal cord stimulation systems may be implanted in the spinal cord to treat chronic pain syndromes, and in the brain to treat refractory chronic pain syndromes, movement disorders, and epilepsy. Peripheral nerve stimulation systems may be used to treat chronic pain syndrome and incontinence. In some cases, paralyzed extremities in spinal cord injury patients may be treated using functional electrical stimulation. Moreover, electrical stimulation systems can be implanted subcutaneously to stimulate subcutaneous tissue, including subcutaneous nerves, such as the occipital nerve.

In general, a stimulator includes a control module (with a pulse generator), a lead, and an array of stimulator electrodes. The stimulator electrodes are placed in contact with or near the nerves, muscles, or other tissue to be stimulated. The pulse generator in the control module generates electrical pulses that are delivered through the electrodes to body tissue. The lead is often anchored at one or more places to prevent or reduce the movement of the lead or stimulator electrodes which could damage tissue, move the stimulator electrodes out of the desired position, or interrupt the connection between the stimulator electrodes and the control module.

Conventionally known lead anchors have shown inadequate lead retention strength and thus result into lead migration, which may further include chances of lead breakage or loose connection. In addition, many conventional anchors provide anchorage to a single lead and thus employment of multiple lead anchors increases overall volume of the implantable stimulation system.

Therefore, there exists a need for a robust lead anchor to secure leads efficiently during stimulation procedures.

BRIEF SUMMARY

One embodiment is a lead anchor including a core housing defining a cavity having a periphery; a swivel anchor disposed in the cavity and having a tubular portion and a locking portion with opposing ends; at least two locking members with at least a portion of each of the locking members disposed within the cavity at the periphery of the cavity; and at least two sleeves with at least a portion of each of the sleeves disposed within the cavity at the periphery of the cavity. The tubular portion is adapted to receive an external tool. The swivel anchor is configured and arranged to rotate within the cavity using the external tool. The lead anchor is configured and arranged to have at least an unlocked configuration, in which the swivel anchor can rotate within the cavity of the core housing without necessarily compressing the sleeves, and a locked configuration, in which the opposing ends of the locking portion of the swivel anchor each lie between one of the sleeves and one of the locking members and compress the sleeves and any lead disposed within the sleeves to hold that lead in place.

Another embodiment is a system including the lead anchor described above and at least one lead configured and arranged for a portion of the at least one lead to be received within at least one of the sleeves of the lead anchor.

Yet another embodiment is a method of implanting an electrical stimulation device. The method including implanting at least one lead near tissue to be stimulated and disposing a lead anchor around a portion of the at least one lead. The lead anchor includes a core housing defining a cavity having a periphery; a swivel anchor disposed in the cavity and having a tubular portion and a locking portion with opposing ends where the tubular portion is adapted to receive an external tool and the swivel anchor is configured and arranged to rotate within the cavity using the external tool; at least two locking members with at least a portion of each of the locking members is disposed within the cavity at the periphery of the cavity; and at least two sleeves carried within the channels with at least a portion of each of the sleeves is disposed within the cavity at the periphery of the cavity. As the lead anchor is disposed around the portion of the lead one lead, the swivel anchor is disposed in an unlocked position. The method also includes rotating the swivel anchor to a locked position in which the opposing ends of the locking portion of the swivel anchor each lie between one of the sleeves and one of the locking members and compress the sleeves and the at least one lead disposed within the sleeves to hold the at least one lead in place of the lead anchor.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DETAILED DESCRIPTION

The present invention is directed to the area of lead anchors used with elongate implantable devices such as spinal cord leads, cardiac pacing leads or catheters, implantable devices or systems containing the lead anchors, methods of use and manufacture of lead anchors and implantable devices. In addition, the present invention is directed to an anchor employing a swivel anchor to secure stimulation leads, and methods of use and manufacture of the lead anchor.

A lead as used herein is a cable including at least one electrical conductor for connecting one or more electrodes disposed on a distal end of the cable, and one or more terminals disposed on one or more proximal ends of the cable. Leads include, for example, percutaneous leads, paddle leads, and cuff leads. Examples of electrical stimulation systems with leads are present in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and 8,364,278, and U.S. Patent Application Publication Serial No. 2007/0150036, all of which are incorporated herein by reference.

In the following sections, embodiments of the present disclosure will be described with reference to a procedure to secure a spinal cord stimulation (SCS) lead with an anchor assembly. It will be understood that this choice is merely exemplary and that the device may be utilized in any other organ, such as deep brain stimulation (DBS), peripheral nerve stimulation (PNS) or any other stimulation that requires securing the leads with the anchor assembly.

Figure 1:
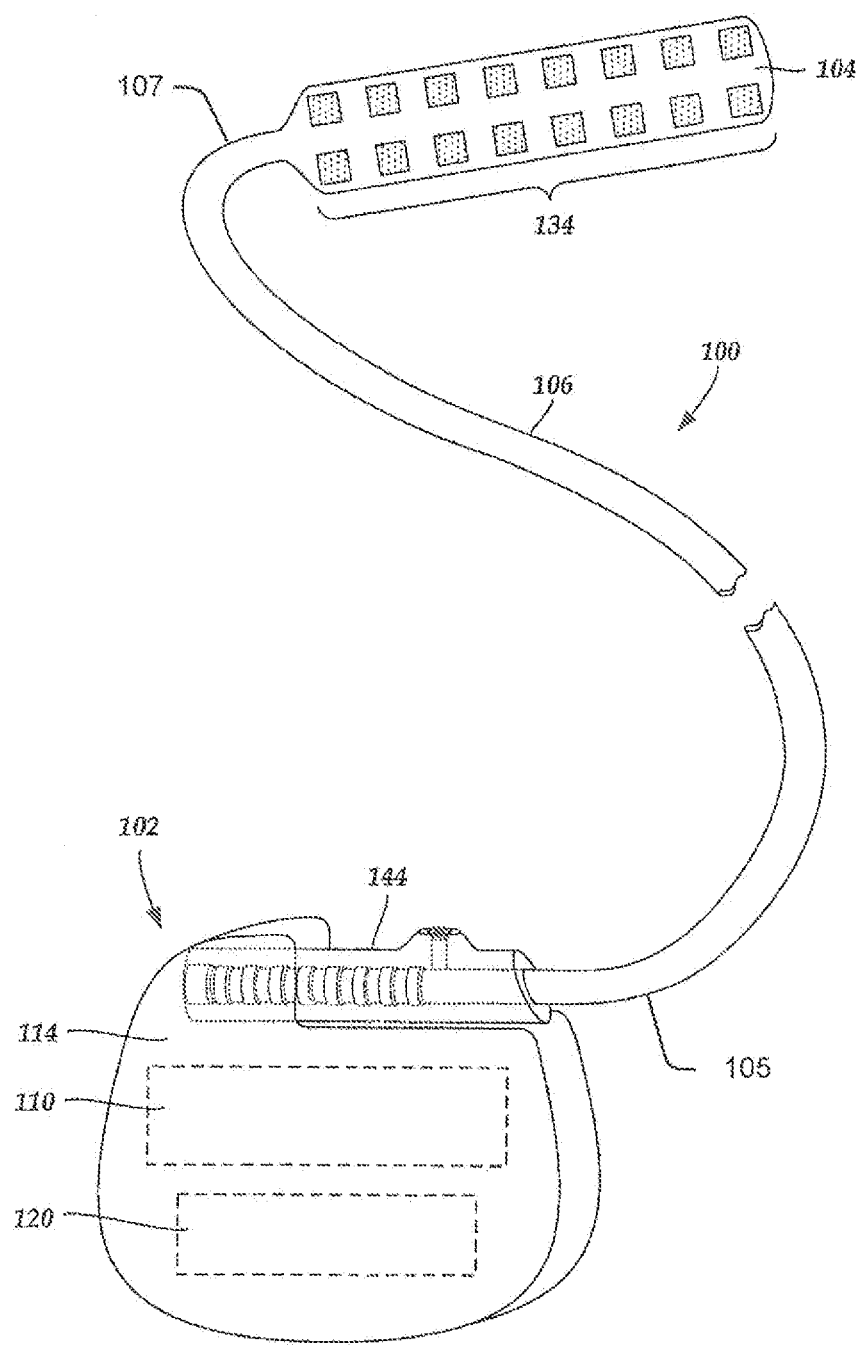
FIG. 1 is a schematic view of one embodiment of an electrical stimulation system, according to the invention.

FIG. 1 is a schematic view of one embodiment of an electrical stimulation system 100. The electrical stimulation system 100 includes a control module (e.g., a stimulator or pulse generator) 102, a paddle body 104, and at least one lead 106, having a proximal end 105 and a distal end 107, coupling the control module 102 to the paddle body 104. The distal end 107 of the lead 106 may include an array of electrodes 134 disposed on the paddle body 104. The control module 102 typically includes an electronic subassembly 110 and an optional power source 120 disposed in a sealed housing 114. The control module 102 typically includes a connector 144 into which the proximal end 105 of the one or more leads 106 can be plugged to make an electrical connection via connector contacts on the control module 102 and terminals (not shown) on each of the one or more leads 106. It should be understood that the electrical stimulation system 100 may include more, fewer, or different components and can have a variety of different configurations including those configurations disclosed in the electrical stimulation system references cited herein. For example, instead of a paddle body 104, the electrodes 134 can be disposed in an array at or near the distal end 107 of the lead 106 forming a percutaneous or isodiametric lead (not shown).

The electrical stimulation system 100 or components of the electrical stimulation system, including one or more of the leads 106, the paddle body 104, and the control module 102, are typically implanted into the body of a patient. The electrical stimulation system 100 can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more leads 106 are typically disposed in, or separated by, a non-conductive, biocompatible material including, for example, silicone, polyurethane, polyetheretherketone, epoxy, and the like, or combinations thereof. The paddle body 104 and one or more leads 106 may be formed in the desired shape by any suitable process including, for example, molding (including, injection molding), casting, and the like. Electrodes and connecting wires can be disposed onto or within a paddle body either prior to or subsequent to a molding or casting process. The non-conductive material typically extends from the distal end of the lead to the proximal end of each of the one or more leads 106. The paddle body 104 and the one or more leads 106 may be a unitary structure or can be formed as separate structures, which may be permanently or detachably coupled.

A lead anchor can be used in an implantable device, such as an implantable spinal cord stimulator, to anchor a lead connecting a control module to an electrode array. The lead anchor includes a fastener, which may be tightened to hold the lead. In at least some embodiments, the lead anchor applies compression to the lead to hold the lead in place.

Figure 2A:
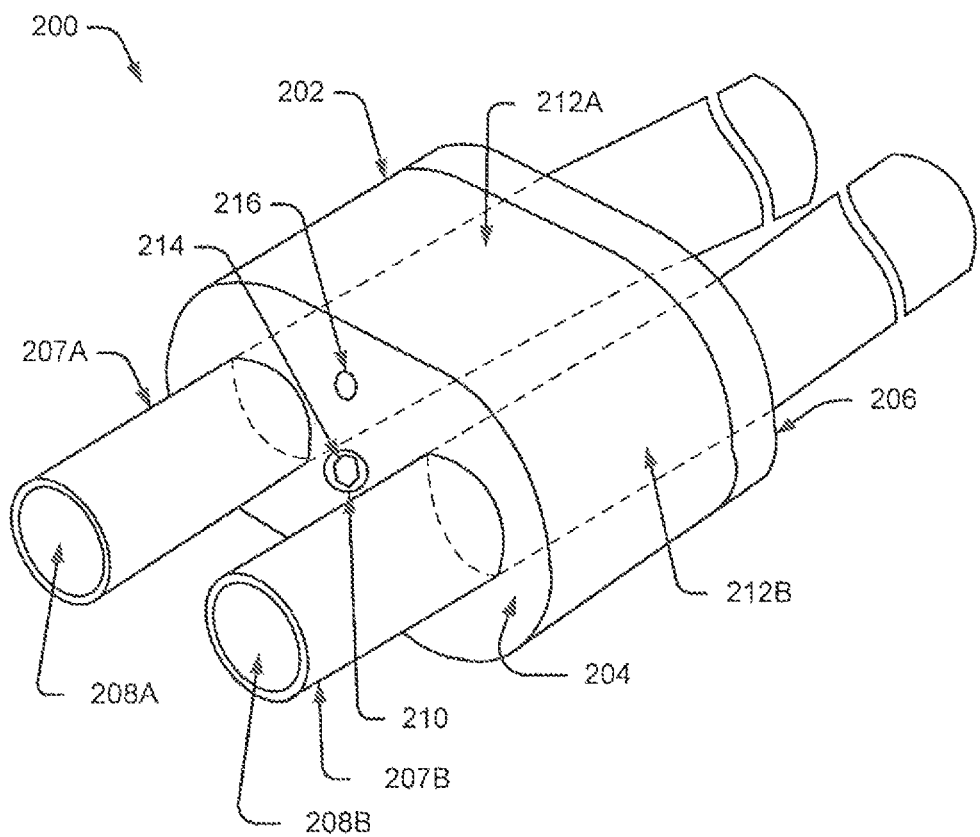
FIGS. 2A and 2B illustrate a lead anchor that may be used to secure leads in the implantable electrical stimulation system of FIG. 1, according to the invention.

FIG. 2A is a schematic view of a portion of one embodiment of a lead anchor 200. Lead anchor 200 can be used to secure at least one lead 106 (FIG. 1) within a patient body. In at least some embodiments, the lead anchor 200 may be employed to secure at least two leads (or two separate elongated portions of a lead) which may provide an effective stimulation for at least two different target sites (not shown). Still further, securing the leads may reduce or avoid dislocation of the lead or leads from the target site.

The lead anchor 200 includes an anchor housing 202 having a proximal portion 204 and a distal portion 206. In one embodiment, the anchor housing 202 may be employed to secure at least one lead 106 (FIG. 1) of the electrical stimulation system 100. The proximal portion 204 includes a first opening 208A, a second opening 208B, and a central opening 210, such that the central opening 210 may be positioned in between the other two openings 208A, 208B. In one embodiment, openings 208A, 208B, and 210 may be parallel, however, other arrangements such as triangular, irregular, or other configurations known to those skilled in the art may also be contemplated.

The first opening 208A and the second opening 208B provide an entrance to sleeves 207A, 207B which define channels 212A, 212B which pass through the anchor housing 202. The sleeves 207A, 207B are arranged to each receive a lead. Leads 106 (FIG. 1) may pass through the channels 212A, 212B and thus across the anchor housing 202. The central opening 210 includes a fitting, such as hex fitting 214, adapted to accept a tool that is used to actuate the locking mechanism of the lead anchor 200. Other configurations known to those skilled in the art, such as a slot or Phillips fitting, can be employed. In at least one embodiment, one or more of the channels 212A, 212B may include a bend to provide a tapered form, which may facilitate insertion of the leads 106 (FIG. 1) within the anchor housing 202. Alternatively, the channels 212A, 212B may be formed in any other suitable configurations such as, but not limited to, straight or irregular configurations. In addition, the anchor housing 202 may also include one or more locking members 216, such as pins, described in more detail below. The anchor housing 202 may be made of a metal, such as titanium, nickel, aluminum, stainless steel, copper, gold, silver, platinum and alloys thereof or any other biocompatible metal, or a rigid plastic or polymer material. The sleeves 207A, 207B may be made of any flexible, biocompatible material including, but not limited to, plastics or other polymer materials.

Figure 2B:
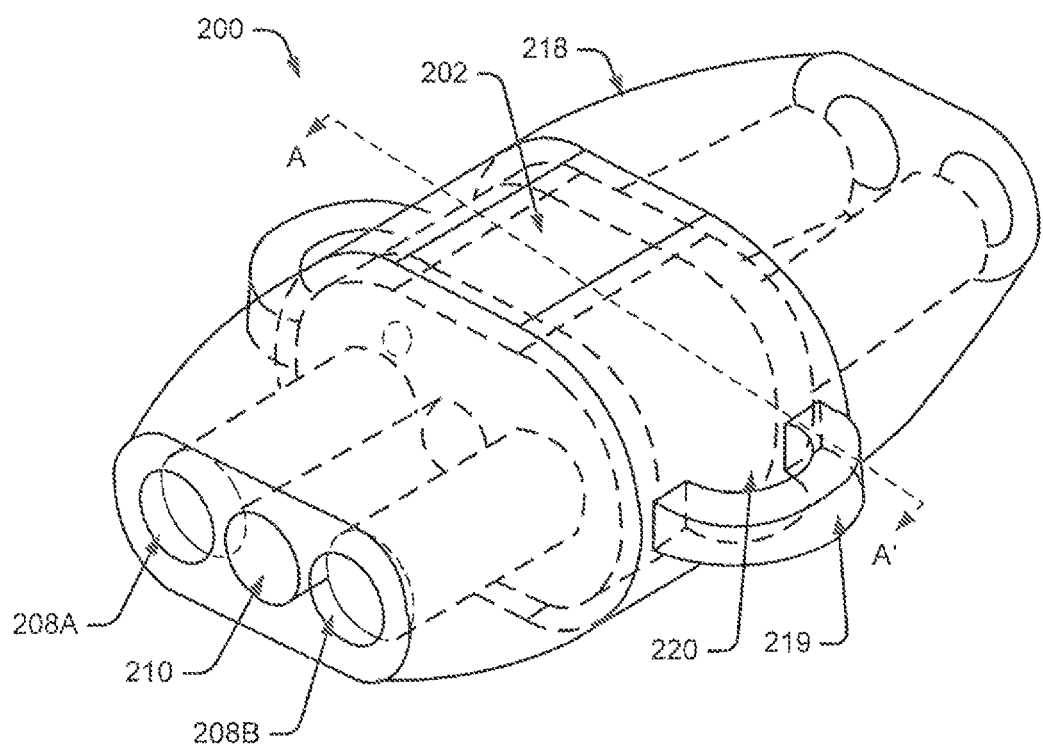

FIG. 2B is schematic view of the lead anchor 200 with the anchor housing 202 be encapsulated in an overmold 218. The overmold 218 may include a case, cover, sheath, or any other suitable structure. In one embodiment, the overmold 218 may be formed of any biocompatible material such as plastics and polymers including, but not limited to, silicone, polyvinyl chloride, fluoropolymers, polyurethane, polycarbonate, acrylic compounds, thermoplastic polyesters, polypropylene, low-density polyethylenes, and other thermoplastic elastomers. In some embodiments, the overmold 218 is made of silicone.

Overmold 218 may provide strain relief to the leads 106 (FIG. a), and it also may safeguard the anchor housing 202 from an applied external force. The overmold 218 may include one or more suture structures 219, such as suture tabs with openings 220, to facilitate suturing the lead anchor 200 to patient tissue.

Figure 3A:
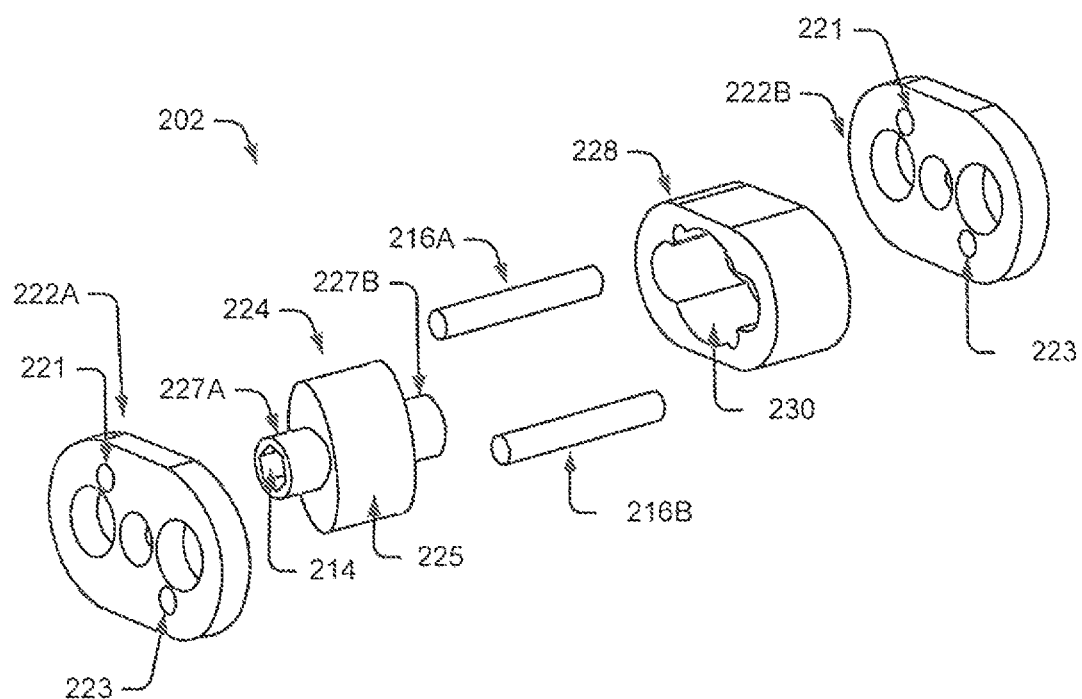
FIG. 3A is an exploded pictorial view of the components of a lead anchor according to the invention.

FIG. 3A is an exploded pictorial view of components of one embodiment of the lead anchor 200. Anchor housing 202 includes endplates 222A, 222B, a swivel anchor 224, locking members 216A, 216B, and core housing 228. The locking members 216A, 216B may include, for example, members such as pins, dowels, screws, bolts, or the like or any other suitable component. The materials employed for manufacturing the components of the anchor housing 202 may include, but are not limited to, stainless steel, titanium, cobalt-nickel alloy, other metals and alloys, rigid plastics, or other suitable biocompatible materials.

Endplates 222A, 222B define the ends of anchor housing 202. In the illustrated embodiment, each endplate is generally rectangular with rounded ends although other suitable shapes can be used. As seen more clearly in FIG. 3C, each endplate 222 (either endplate 22A or endplate 22B of FIG. 3A) includes two openings 208A, 208B formed lying on either side of a central opening 210. The three openings 208A, 208B, 210 may lie generally on the vertical centerline of the element, with central opening 210 horizontally centered as well. Apertures 221,223 are formed above and below the openings 208A, 208B, 210, and these apertures may be sized to accommodate locking members 216A, 216B.

Core housing 228 forms the center of anchor housing 202 and provides a support structure for other components in a sandwich-shaped configuration, with endplates 222A, 222B lying on either side of the core housing 228. Core housing 228 defines a cavity 230 to accommodate the swivel anchor 224 and locking members 216A, 216B, as discussed in detail below. The configuration of core housing 228 and cavity 230 are influenced by these elements.

Swivel anchor 224 locks leads 106 (FIG. 1) in place within core housing 228. The swivel anchor 224 includes a solid, paddle-shaped locking portion 225, with one or two tubular portions 227A, 227B extending longitudinally from the same. In at least some embodiments, locking portion 225 presents a generally flattened form with curved surfaces (e.g., a form with an oval-shaped transverse cross-section) extending transversely within core housing 228. The ends of locking portion 225 may form narrowed, rounded features. Tubular portions 227A, 227B extend longitudinally from the sides of the locking portion 225, generally on the locking portion's axis of rotation.

In one embodiment, the tubular portion 227A includes a fitting 214 suitable to receive a tool, such as a hex tool or a slotted or Phillips tool. With fitting 214, an operator can use a suitable tool to turn the swivel anchor 224 within core housing 228. For example, the fitting 214 may receive a tip of a torque wrench which can then be used to rotate the swivel anchor to lock one or more leads in place.

Figure 3B:
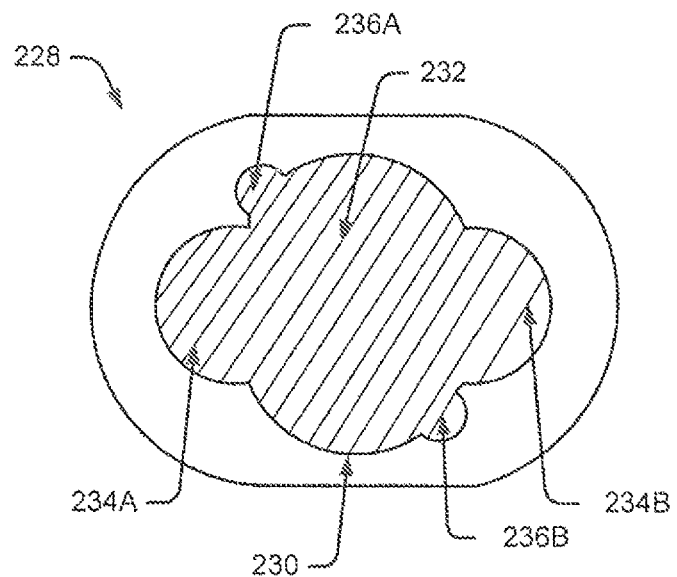
FIGS. 3B and 3C are front views of components of a lead anchor according to the invention.
Figure 3C:
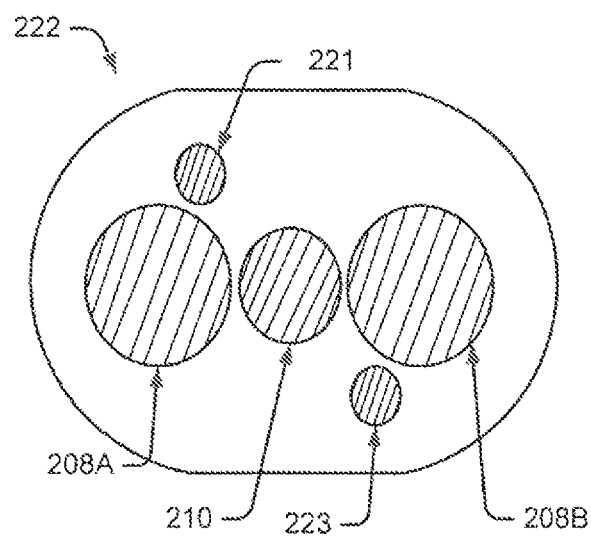

The configuration of core housing 228 can be understood in relation to the components assembled within that element. As shown in FIG. 3B, core housing 228 defines a complex inner cavity 230. That cavity results from a combination of a number of individual, simpler openings. A central bore 232 lies on the central axis of core housing 228 and is generally circular with a diameter sufficient to accommodate the locking portion 225 of the swivel anchor 224. Overlapping the central bore are two lead bores 234A, 234B lying on the vertical centerline of core housing 228 and sized to receive a portion of each sleeves 207A, 207B, respectively (see FIG. 2A). Locking member bores 236A, 236B also overlap central bore 232 and are located generally clockwise around the circumference of central bore 232 from the lead bores 234A, 234B. These bores are sized to accept a portion of each locking member 216A, 216B, respectively.

The components shown in FIG. 3A may be assembled by fitting an end plate 222A over the central cavity 230 and inserting the swivel anchor 224, sliding the tubular portion 227A into the central opening 210. The other end plate 222B is then attached and the locking members 216A, 216B are inserted.

Alternatively, the swivel anchor 224 have any other suitable shape, which may include an elliptical shape, an oval shape, or the like. The manufacturing of the anchor housing 202 may include machining processes such as, but not limited to, lathing, milling, drilling, cutting, and so forth. In at least some embodiments, components of the anchor housing 202 may be manufactured by stamping, laser cutting, wire electromachining, sintering, or any other suitable mechanical process or combinations thereof.

Components illustrated in FIG. 3A may be combined in a number of configurations to obtain a functioning anchor housing 202. For instance, in an exemplary embodiment, one end plate 222B and core housing 228 may be formed as a single unit. In yet another embodiment, locking members 216A, 216B may be formed with the core housing 228 as a single unit.

Figure 4A:
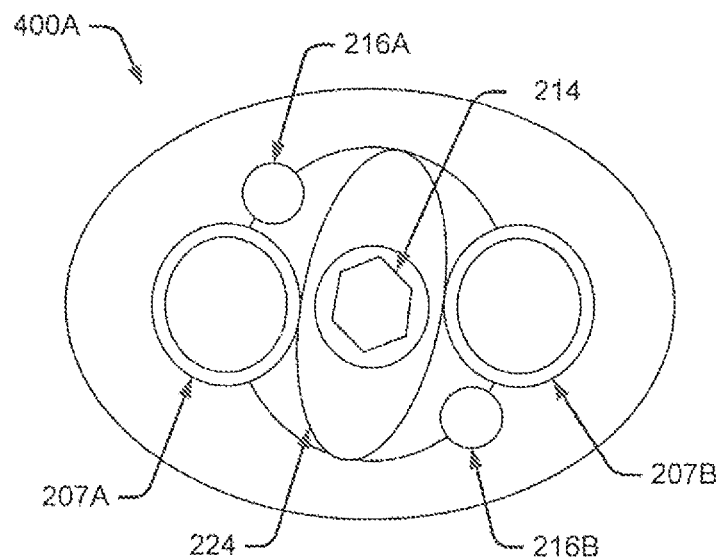
FIGS. 4A, 4B, and 4C are cross-sectional views taken on plane A-A' of FIG. 2B of the lead anchor in unlocked, intermediate, and locked configurations, respectively; according to the invention.
Figure 4B:
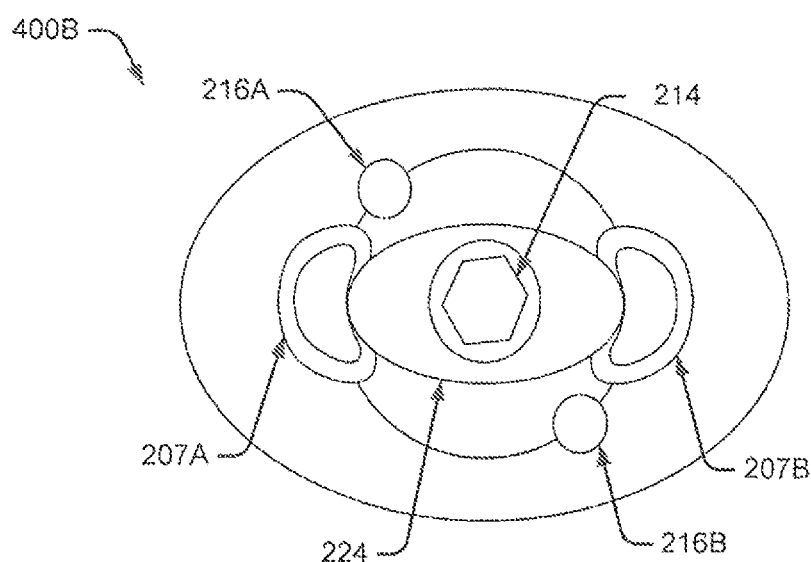
Figure 4C:
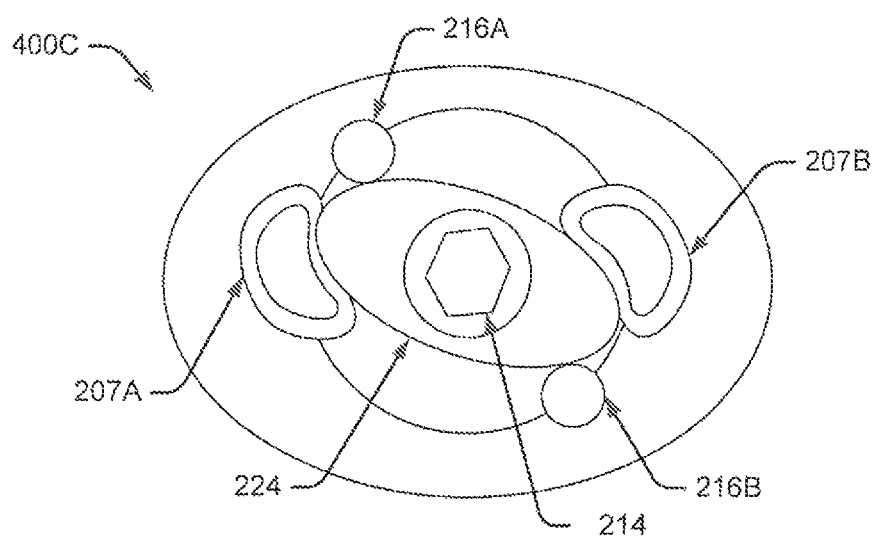

FIGS. 4A, 4B, and 4C are cross-sectional views of the lead anchor 200 in unlocked, intermediate, and locked configurations, respectively. In the unlocked configuration 400A, the swivel anchor 224 rests within the cavity 230. In this unlocked configuration 400A of FIG. 4A, the swivel anchor 224 can rotate within central cavity 230 without necessarily bearing on the leads 106 or sleeves 207A, 207B. Thus, leads 106 may move freely within the sleeves 207A, 207B, which are not compressed by the swivel anchor 224. Upon rotation of the swivel anchor 224 (in a clockwise direction for the illustrated embodiment), the lead anchor 200 assumes an intermediate configuration 400B of FIG. 4B where the swivel anchor 224 compresses the sleeves 207A, 207B and exerts pressure on the portions of the leads 106 disposed in the sleeves. This intermediate configuration 400B lies in an unstable equilibrium. Further rotation of the swivel anchor 224 results in the stable locked configuration 400C of FIG. 4C. Prior to reaching the intermediate configuration 400B, the swivel anchor 224 will rotate toward the unlocked position. Once the swivel anchor 224 passes the point of maximum compression of sleeves 207A, 207B, the swivel anchor 224 with rotate toward the stable locked configuration 400C. In the locked configuration 400C, the swivel anchor 224 is urged against the locking members 216A, 216B by the sleeves 207A, 207B and the leads 106 residing in the sleeves. The swivel anchor 224 is thus locked in a stable configuration 400C, which secures the leads 106 within the sleeves 207A, 207B. When the lead anchor 200 is then attached to patient tissue, the leads are then anchored in position within the patient.

Figure 5:
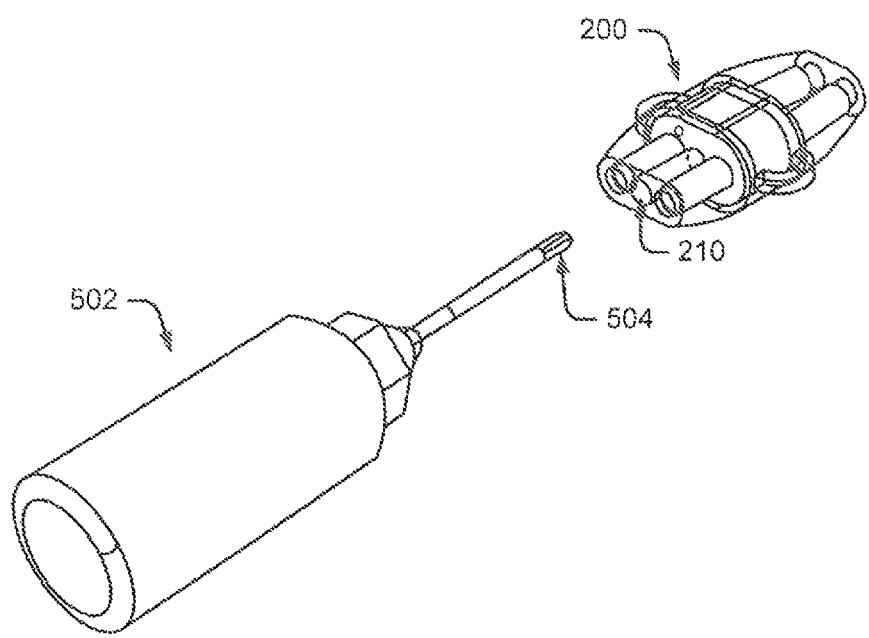
FIG. 5 illustrates a method of using the lead anchor employing a tool, according to the invention.

FIG. 5 is a perspective view illustrating the lead anchor 200 being engaged by a tool 502. Leads 106 (not shown) may be inserted through the lead anchor 200. In one embodiment, a tool 502 is employed to secure the leads 106. The tool 502 may be, for example, a torque wrench 502 or other suitable tool adapted to engage the fitting 214.

The lead anchor 200 of FIG. 2B may receive a pair of leads 106 (not shown). Initially, leads 106 are placed in position to achieve the desired paresthesia at the chosen site of stimulation. In at least some embodiments, the leads are inserted into the sleeves 207A, 207B and carried in the channels 212A, 212B of the anchor housing 202. The lead anchor 200 is slid along the length of the leads until it is in the desired position for anchoring to the ligament or fascia. After the leads have been positioned, the tool 502 engages the fitting 214 of the lead anchor 202. The distal end of the tool 502 includes a head 504 shaped to engage the fitting 214 (FIG. 4C). The user inserts the distal end of the tool 502 into the central opening 210 to engage the fitting 214 (not shown) of swivel anchor 224. Further, the user provides sufficient torque at the proximal end of the torque wrench 502 to rotate the swivel anchor 224 (see FIGS. 4A-C). The rotation of swivel anchor 224 moves the swivel anchor to the intermediate configuration 400B, which may provide for the maximum compression to leads 106. Continued rotation moves the swivel anchor 224 to the stable locked configuration 400C with the swivel anchor 224 abutting both the sleeves 207A, 207B and the locking members 216A, 216B, thus securing the leads 106 within the lead anchor 200. In at least some embodiments, the user may rotate the fitting 214 in the opposite direction to cause the swivel anchor 224 to move to the unlocked configuration 400A, thereby freeing the leads 106.

Embodiments of the present disclosure may be used in any medical or non-medical procedure, including any medical procedure where one or more body part receive electrical stimulation. In addition, at least certain aspects of the aforementioned embodiments may be combined with other aspects of the embodiments, or removed.

While the present disclosure has been described by means of specific embodiments and applications thereof, numerous modifications and variations could be made thereto by those skilled in the art without departing from the scope of the present disclosure set forth in the claims.

What is claimed is:

1. A lead anchor, comprising:
   a core housing defining a cavity having a periphery;
   a swivel anchor disposed in the cavity and comprising a tubular portion and a locking portion with opposing ends, the tubular portion adapted to receive an external tool, wherein the swivel anchor is configured and arranged to rotate within the cavity using the external tool;
   at least two locking members, wherein at least a portion of each of the locking members is disposed within the cavity at the periphery of the cavity; and
   at least two sleeves, wherein at least a portion of each of the sleeves is disposed within the cavity at the periphery of the cavity;
   wherein the lead anchor is configured and arranged to have at least an unlocked configuration, in which the swivel anchor can rotate within the cavity of the core housing without necessarily compressing the sleeves, and a locked configuration, in which the opposing ends of the locking portion of the swivel anchor each lie between one of the sleeves and one of the locking members and compress the sleeves and any lead disposed within the sleeves to hold that lead in place.

2. The lead anchor of claim 1, wherein the locking members are pins.

3. The lead anchor of claim 1, further comprising a flexible overmold disposed over the core housing.

4. The lead anchor of claim 1, wherein the swivel anchor further comprises a fitting disposed in the tubular portion to receive a tip of the external tool.

5. The lead anchor of claim 4, wherein the fitting is a hex fitting.

6. The lead anchor of claim 1, wherein the sleeves are flexible.

7. The lead anchor of claim 1, wherein the core housing is formed of a material selected from a metal, alloy, rigid plastic, or any combination thereof.

8. The lead anchor of claim 1, wherein the locking portion of the swivel anchor has an oval transverse cross-section.

9. The lead anchor of claim 1, wherein the at least two locking members are exactly two locking members disposed diagonally from each other at the periphery of the cavity.

10. The lead anchor of claim 1, wherein the lead anchor further comprises at least one endplate attached to the core housing.

11. A system, comprising:
    the lead anchor of claim 1; and
    at least one lead configured and arranged for a portion of the at least one lead to be received within at least one of the sleeves of the lead anchor.

12. The system of claim 11, wherein the at least one lead is at least two leads, wherein the lead anchor is configured and arranged so that a portion of each of the two leads is received in a different one of the sleeves.

13. The system of claim 11, further comprising a control module coupleable to the at least one lead and configured and arranged to provide electrical stimulation pulses to the at least one lead.

14. A method of implanting an electrical stimulation device, the method comprising:
    implanting at least one lead near tissue to be stimulated;
    disposing a lead anchor around a portion of the at least one lead, the lead anchor comprising a core housing defining a cavity having a periphery; a swivel anchor disposed in the cavity and comprising a tubular portion and a locking portion with opposing ends, the tubular portion adapted to receive an external tool, wherein the swivel anchor is configured and arranged to rotate within the cavity using the external tool; at least two locking members, wherein at least a portion of each of the locking members is disposed within the cavity at the periphery of the cavity; and at least two sleeves carried within the channels, wherein at least a portion of each of the sleeves is disposed within the cavity at the periphery of the cavity, wherein as the lead anchor is disposed around the portion of the lead one lead, the swivel anchor is disposed in an unlocked position; and
    rotating the swivel anchor to a locked position in which the opposing ends of the locking portion of the swivel anchor each lie between one of the sleeves and one of the locking members and compress the sleeves and the at least one lead disposed within the sleeves to hold the at least one lead in place of the lead anchor.

15. The method of claim 14, wherein disposing a lead anchor around a portion of the at least one lead comprises disposing the portion of the at least one lead into a one of the sleeves.

16. The method of claim 14, wherein rotating the swivel anchor comprises engaging a fitting disposed in the tubular portion of the swivel anchor with a tool and using the tool to rotate the swivel anchor into the locked position.

17. The method of claim 14, wherein implanting at least one lead and disposing a lead anchor around a portion of the at least one lead comprises implanting two leads and disposing the lead anchor around portion of the two leads.

18. The method of claim 14, further comprising rotating the swivel anchor from the locked position to the unlocked position to release the at least one lead.

19. The method of claim 14, wherein disposing a lead anchor around a portion of the at least one lead comprises sliding the lead anchor onto the at least one lead.

20. The method of claim 14, further comprising coupling the at least one lead to a control module and implanting the control module.

* * * * *